United States Patent [19]

Nijkerk et al.

[11] Patent Number: 5,104,896

[45] Date of Patent: Apr. 14, 1992

[54] CARBOPLATIN COMPOSITION

[75] Inventors: Alfred J. Nijkerk, Amsterdam; Johanna M. P. Vermeer, Lisse, both of Netherlands

[73] Assignee: Pharmachemie B.V., Haarlem, Netherlands

[21] Appl. No.: 529,917

[22] Filed: May 29, 1990

[30] Foreign Application Priority Data

Jun. 6, 1989 [NL] Netherlands ............ 8901433

[51] Int. Cl.$^5$ .............................................. A61K 31/28
[52] U.S. Cl. ................................................... 514/492
[58] Field of Search ........................................ 514/492

[56] References Cited

U.S. PATENT DOCUMENTS

| 4,339,437 | 7/1982 | Rosenberg et al. | 424/649 |
| 4,687,780 | 8/1987 | Barnard | 514/492 |
| 4,873,226 | 10/1989 | Talroy et al. | 514/492 |

FOREIGN PATENT DOCUMENTS

| 0143478 | 6/1985 | European Pat. Off. | 424/649 |
| 275559 | 7/1988 | European Pat. Off. | 514/492 |

OTHER PUBLICATIONS

Chemical Abstracts, vol. 52, cols. 4113-4114.

Primary Examiner—Jerome D. Goldberg
Attorney, Agent, or Firm—Ladas & Parry

[57] ABSTRACT

A carboplatin composition is provided in the form of an aqueous solution of carboplatin buffered at a pH of 2-6.5. Such a ready to use solution possesses a remarkable stability.

10 Claims, No Drawings

CARBOPLATIN COMPOSITION

BACKGROUND OF THE INVENTION

Carboplatin is a known cytostatic agent. Up till now, this agent was marketed as a freeze-dried product and accordingly it is reconstituted before administration. Of course, a ready to use solution would be a much more advantageous composition, but carboplatin is not stable in a simple aqueous solution. As has appeared by research, carboplatin can decompose through various mechanisms, whereby a.o. the highly poisonous compounds di-µ-hydroxo-bis(cis-diammineplatinum (II)), and tri-µ-hydroxo-tris(cis-diammineplatinum (II)) can be formed.

SUMMARY OF THE INVENTION

It has now been found that a solution buffered in a certain pH range is sufficiently stable to be used as carboplatin composition.

Accordingly, the invention provides a carboplatin composition which is characterized by the fact that it has the form of an aqueous solution of carboplatin which has been buffered at a pH of 2-6.5.

DESCRIPTION OF PREFERRED EMBODIMENTS

In the upper part of the above mentioned range the stability is acceptable, but it is even better at a somewhat lower pH. Furthermore, the injection of the solution is of course more disagreeable, the lower the pH is. Consequently, the solution is preferably buffered at a pH of 2.5-4.5 and more preferably at a pH of 3.1-3.5.

The maximum solubility of the carboplatin is about 22 mg/ml. The concentration of the preparation of the present invention can be adjusted arbitrarily up to this limit; usually a therapeutical concentration is used of 8-12 mg/ml, particularly around 10 mg/ml.

One can use any buffering agent, for instance those mentioned in Handbook of Chemistry and Physics, 58th Edition, pages D-133 to D-135, which is incorporated herein by reference.

For practical reasons one can suitably use a phosphate buffer, with which, as is well known, the pH can be adjusted within a very broad range.

It is prefered to have the lowest possible buffer concentration which however, should have sufficient buffering capacity. Generally, a strength of the buffer of about 0.01-0.03M will suffice.

For completeness' sake it is remarked that from EP-A-0 275 559 a cytostatic agent on the basis of carboplatin is known, which has a specific distribution of particle sizes and is prepared according to a very special process. From this powdery product injectable solutions can be made, but according to page 4, lines 31-34 these solutions should contain further adjuvants and should be made up immediately before use. The same appears from the last paragraph of example 4 of this publication.

The following, non-limiting example further elucidates the present invention.

A series of carboplatin solutions having a concentration of 10 mg/ml was prepared with the following buffers and pH-values:

1: Carboplatin in 0.01M sodium-di-hydrogen phosphate, pH 2.5 with phosphoric acid.
2-1: Carboplatin in 0.01M sodium-di-hydrogen phosphate, pH 3.5 with phosphoric acid.
2-2: Carboplatin in 0.10M sodium-di-hydrogen phosphate, pH 3.5 with phosphoric acid.
2-3: Carboplatin in 0.50M sodium-di-hydrogen phosphate, pH 3.5 with phosphoric acid.
3: Carboplatin in 0.01M sodium-di-hydrogen phosphate, pH 4.5 with phosphoric acid.
4: Carboplatin in 0.01M di-sodium-hydrogen phosphate, pH 5.5 with phosphoric acid.
5: Carboplatin in 0.01M di-sodium-hydrogen phosphate, pH 6.5 with phosphoric acid.
6: Carboplatin in 0.01M di-sodium-hydrogen phosphate, pH 7.5 with sodium hydroxide.

The above mentioned solutions were stored during 1, 2, 3 and 4 months under the following conditions:

| | |
|---|---|
| A | 0-8° C. |
| B | 20-22° C. (room temperature) |
| C | 40° C. |

The pH of each solution was measured and the contents of carboplatin and decomposition products were determined by liquid chromatography. This was done with the solution as originally prepared, and after 1, 2, 3 and 4 months. The results are given in the following tables. For the sake of brevity the content of decomposition products has been indicated therein as "by-peaks".

| | Original | | | 1 month | | | 2 months | | | 3 months | | | 4 months | | |
|---|---|---|---|---|---|---|---|---|---|---|---|---|---|---|---|
| Solutions | content | by peaks | pH | content | by peaks | pH | content | by peaks | pH | content | by peaks | pH | content | by peaks | pH |
| Results at 0-8° C. | | | | | | | | | | | | | | | |
| 1: pH 2.5 | 100% | 1.5% | 2.50 | 98.5% | 1.0% | 2.78 | 96.3% | 1.8% | 2.76 | 97.4% | 1.4% | 2.76 | 98.1% | 1.8% | 2.81 |
| 2-1: pH 3.5 | 100% | 0.8% | 3.50 | 99.5% | 0.4% | 3.88 | 97.8% | 0.8% | 3.88 | 98.1% | 0.9% | 3.93 | 98.2% | 1.2% | 4.01 |
| 2-2: pH 3.5 | 100% | 0.6% | 3.50 | 98.2% | 0.6% | 3.62 | 96.7% | 1.3% | 3.61 | 97.0% | 1.4% | 3.63 | 95.2% | 2.4% | 3.72 |
| 2-3: pH 3.5 | 100% | 1.2% | 3.50 | 96.4% | 1.4% | 3.56 | 93.4% | 2.1% | 3.53 | 92.2% | 2.5% | 3.55 | 90.7% | 3.2% | 3.62 |
| 3: pH 4.5 | 100% | 0.5% | 4.50 | 99.3% | 0.2% | 5.01 | 96.7% | 0.8% | 5.07 | 98.1% | 1.2% | 5.20 | 98.9% | 1.5% | 5.18 |
| 4: pH 5.5 | 100% | 0.4% | 5.50 | 99.3% | 0.3% | 5.50 | 98.2% | 0.8% | 5.47 | 97.8% | 1.4% | 5.53 | 98.8% | 1.6% | 5.57 |
| 5: pH 6.5 | 100% | 0.5% | 6.50 | 99.6% | 0.3% | 6.44 | 97.4% | 1.2% | 6.38 | 97.3% | 1.7% | 6.39 | 98.1% | 2.2% | 6.45 |
| 6: pH 7.5 | 100% | 0.7% | 7.50 | 99.0% | 1.0% | 7.38 | 95.7% | 2.1% | 7.25 | 94.7% | 3.2% | 7.25 | 93.7% | 4.2% | 7.30 |
| Results at room temperature | | | | | | | | | | | | | | | |
| 1: pH 2.5 | 100% | 1.5% | 2.50 | 99.3% | 1.3% | 2.77 | 97.2% | 1.9% | 2.77 | 98.9% | 2.0% | 2.76 | 98.7% | 2.9% | 2.82 |
| 2-1: pH 3.5 | 100% | 0.8% | 3.50 | 99.7% | 0.6% | 3.88 | 98.0% | 1.0% | 3.91 | 99.6% | 1.4% | 3.97 | 99.2% | 2.3% | 4.08 |
| 2-2: pH 3.5 | 100% | 0.6% | 3.50 | 97.0% | 1.2% | 3.64 | 95.6% | 1.6% | 3.62 | 96.6% | 1.7% | 3.64 | 96.4% | 2.7% | 3.74 |
| 2-3: pH 3.5 | 100% | 1.2% | 3.50 | 91.7% | 3.0% | 3.58 | 89.7% | 3.0% | 3.54 | 90.5% | 3.0% | 3.55 | 89.9% | 3.8% | 3.63 |
| 3: pH 4.5 | 100% | 0.5% | 4.50 | 99.3% | 0.5% | 5.03 | 97.1% | 1.0% | 5.03 | 98.6% | 1.4% | 5.15 | 99.0% | 1.7% | 5.2 |
| 4: pH 5.5 | 100% | 0.4% | 5.50 | 98.8% | 0.7% | 5.44 | 96.7% | 1.2% | 5.43 | 98.7% | 1.6% | 5.47 | 98.3% | 2.0% | 5.55 |
| 5: pH 6.5 | 100% | 0.5% | 6.50 | 98.1% | 1.2% | 6.36 | 95.2% | 1.6% | 6.29 | 96.4% | 2.6% | 6.32 | 95.8% | 3.4% | 6.37 |
| 6: pH 7.5 | 100% | 0.7% | 7.50 | 94.8% | 3.3% | 7.16 | 89.9% | 3.9% | 7.02 | 89.8% | 4.3% | 7.02 | 89.1% | 5.0% | 7.04 |

-continued

| Solutions | Original | | | 1 month | | | 2 months | | | 3 months | | | 4 months | | |
|---|---|---|---|---|---|---|---|---|---|---|---|---|---|---|---|
| | content | by peaks | pH | content | by peaks | pH | content | by peaks | pH | content | by peaks | pH | content | by peaks | pH |
| Results at 40° C. | | | | | | | | | | | | | | | |
| 1: pH 2.5 | 100% | 1.5% | 2.50 | 97.4% | 2.1% | 2.89 | 93.8% | 4.1% | 2.82 | 95.2% | 4.0% | 2.86 | 94.5% | 5.3% | 2.93 |
| 2-1: pH 3.5 | 100% | 0.8% | 3.50 | 98.3% | 1.4% | 4.10 | 95.4% | 2.4% | 4.35 | 96.6 | 2.6% | 4.58 | 96.1% | 3.7% | 4.71 |
| 2-2: pH 3.5 | 100% | 0.6% | 3.50 | 95.8% | 1.9% | 3.66 | 93.3% | 2.8% | 3.68 | 93.5 | 3.3% | 3.74 | 92.8% | 4.6% | 3.84 |
| 2-3: pH 3.5 | 100% | 1.2% | 3.50 | 89.0% | 4.1% | 3.96 | 87.7% | 3.7% | 3.53 | 87.3% | 4.2% | 3.59 | 86.5% | 5.7% | 3.65 |
| 3: pH 4.5 | 100% | 0.5% | 4.50 | 98.2% | 1.3% | 5.08 | 94.6% | 3.7% | 5.22 | 96.3% | 2.7% | 5.32 | 95.7% | 3.1% | 5.4 |
| 4: pH 5.5 | 100% | 0.4% | 5.50 | 97.8% | 1.5% | 5.41 | 94.4% | 3.3% | 5.43 | 96.4% | 2.6% | 5.48 | 95.2% | 3.2% | 5.55 |
| 5: pH 6.5 | 100% | 0.5% | 6.50 | 95.7% | 2.7% | 6.25 | 93.3% | 3.5% | 6.22 | 93.7% | 3.5% | 6.25 | 93.3% | 3.7% | 6.29 |
| 6: pH 7.5 | 100% | 0.7% | 7.50 | 88.9% | 5.8% | 6.93 | 85.9% | 5.8% | 6.90 | 86.0% | 5.6% | 7.60 | 85.5% | 5.8% | 6.84 |

It appears from the above results that a too high concentration of buffering agent has an adverse influence on the stability (solution 2-3). For the rest the solutions appear to be well stable in the pH range up to and inclusive 6.5, even at 40° C.

What we claim is:

1. Carboplatin composition, which has the form of an aqueous solution of carboplatin, which has been buffered with a suitable buffering agent at a pH of 2-6.5, said carboplatin being present in said solution in a therapeutic concentration not exceeding 22 mg/ml, said buffering agent having a concentration of about 0.01-0.1M.

2. Carboplatin composition according to claim 1, which has been buffered at a pH of 2.5-4.5.

3. Carboplatin composition according to claim 2, which has been buffered at a pH of 3.1-3.5.

4. Carboplatin composition according to claim 1, wherein the buffering agent is a phosphate buffer.

5. Carboplatin composition according to claim 2, wherein the buffering agent is a phosphate buffer.

6. Carboplatin composition according to claim 3, wherein the buffering agent is a phosphate buffer.

7. Carboplatin composition according to claim 1, wherein the buffering agent has a concentration of 0.01-0.3M.

8. Carboplatin composition according to claim 2, wherein the buffering agent has a concentration of 0.01-0.3M.

9. Carboplatin composition according to claim 3, wherein the buffering agent has a concentration of 0.01-0.3M.

10. Carboplatin composition according to claim 1, wherein the carboplatin concentration is 8-12 mg/ml.

* * * * *